United States Patent [19]

Kramer et al.

[11] Patent Number: 4,560,825

[45] Date of Patent: Dec. 24, 1985

[54] ADAMANTANE DERIVATIVE/SURFACTANT CATALYZED PARAFFIN-OLEFIN ALKYLATION

[75] Inventors: George M. Kramer, Berkeley Heights; Edwin R. Ernst, Belle Mead, both of N.J.

[73] Assignee: Exxon Research & Engineering Company, Florham Park, N.J.

[21] Appl. No.: 682,787

[22] Filed: Dec. 18, 1984

Related U.S. Application Data

[63] Continuation-in-part of Ser. No. 599,532, Apr. 12, 1984, abandoned, which is a continuation-in-part of Ser. No. 540,120, Oct. 7, 1983, abandoned.

[51] Int. Cl.[4] .................................................. C07C 2/58
[52] U.S. Cl. ..................................... 585/724; 585/726; 585/728; 585/730; 585/731
[58] Field of Search ............... 585/725, 724, 726, 728, 585/730, 731

[56] References Cited

U.S. PATENT DOCUMENTS

| | | | |
|---|---|---|---|
| 3,310,469 | 3/1967 | Paulshock et al. | 424/180 |
| 3,324,196 | 6/1967 | Kramer et al. | 585/725 |
| 3,551,514 | 12/1970 | Evering | 585/731 |
| 3,671,598 | 6/1972 | Moore | 585/350 |
| 3,829,525 | 8/1974 | Cole et al. | 585/725 |
| 3,839,490 | 10/1974 | Schneider | 585/743 |

*Primary Examiner*—Curtis R. Davis
*Attorney, Agent, or Firm*—Henry E. Naylor

[57] ABSTRACT

Disclosed is an alkylation process comprising the step of contacting a paraffinic compound, capable of forming a carbonium ion under strong acid conditions, with an olefin in the presence of a strong acid system comprised of an acid component and a mixture comprised of: (a) one or more adamantane derivatives containing at least one unsubstituted bridgehead position and which is capable of being protonated, or hydrogen bonded to, or dissociated by an acid; and (b) one or more surfactants capable of stabilizing the one or more adamantane derivatives of (a) above at a hydrocarbon-acid interface.

4 Claims, 2 Drawing Figures

FIG.1

FIG.2 ved product quality in terms of motor octane number and yield. Specifically, what is desired is a process which inhibits the side reaction of "cracking", which involves the catalytic degradation of the desired product, $C_8$ branched hydrocarbons, to other hydrocarbons which are not as useful for octane improvement.

ADAMANTANE DERIVATIVE/SURFACTANT CATALYZED PARAFFIN-OLEFIN ALKYLATION

CROSS-REFERENCE TO RELATED APPLICATIONS

This application is a continuation-in-part application of U.S. Ser. No. 599,532, filed Apr. 12, 1984, which is a continuation-in-part of U.S. Ser. No. 540,120, filed Oct. 7, 1983 both of which are now abandoned.

BACKGROUND OF THE INVENTION

1. Field of the Invention

This invention relates to a process is for paraffin-olefin alkylation producing highly branched paraffins under strong acid catalyzed conditions and in the presence of a mixture of an adamantane derivative and a surfactant as a combination surfactant/hydride transfer catalyst.

2. Brief Description of the Prior Art

The alkylation of olefins with isobutane, which proceeds by the addition of carbonium ions to the olefins under strong acid conditions, is a well-known process in the art for producing a wide variety of useful hydrocarbon materials and particularly, gasoline blending components. For example, 2,2,4-trimethylpentane is a common blending component which is used for octane improvement of motor gasoline and can be produced by alkylating butenes with isobutane in sulfuric acid or liquid HF. An example of such an acid catalyzed reaction process is described in U.S. Pat. No. 3,231,633.

Further examples of acid-catalyzed hydrocarbon conversion processes employing novel Lewis acid systems are disclosed in U.S. Pat. No. 4,229,611 and U.S. Pat. No. 4,162,233, both assigned to Exxon Research and Engineering Company.

In a related case, U.S. Pat. No. 3,671,598 describes a process for isomerizing saturated cyclic hydrocarbons under strong acid conditions in the presence of an adamantane hydrocarbon.

Further, U.S. Pat. Nos. 4,357,481; 4,357,484; 4,357,482; and 4,357,483 to George M. Kramer (issued Nov. 2, 1982, and assigned to Exxon Research and Engineering Company) disclose the use of adamantane hydrocarbons in paraffin-olefin alkylation and non-cyclic paraffin isomerization, and the use of aminoalkyladamantanes in paraffin-olefin alkylation and non-cyclic paraffin isomerization, respectively, in which rates of reaction are substantially increased as compared to those obtained in the absence of the specifically disclosed adamantane.

There is a constant search in the art for discovering processes for producing alkylated paraffinic hydrocarbons such as $C_8$ branched hydrocarbons, which are currently used as octane improvement agents. These desired processes should preferably increase product quality and process economy and efficiency, factors which are reflected in terms of fewer side reactions, less acid catalyst consumption and faster desirable reaction rates. Overall, these process parameters result in improved product quality in terms of motor octane number and yield. Specifically, what is desired is a process which inhibits the side reaction of "cracking", which involves the catalytic degradation of the desired product, $C_8$ branched hydrocarbons, to other hydrocarbons which are not as useful for octane improvement.

SUMMARY OF THE INVENTION

In accordance with the present invention there is provided an alkylation process comprising the step of contacting a paraffinic compound, capable of forming a carbonium ion under strong acid conditions, with an olefin, in the presence of a strong acid system containing an acid component and a mixture comprised of: (a) an adamantane derivative containing at least one unsubstituted bridgehead position and which is capable of being protonated, or hydrogen bonded to, or dissociated by, the acid, yielding an adamantyl species which is soluble in the acid throughout the alkylation reaction; and (b) a surfactant capable of stabilizing the adamantyl species at the acid-hydrocarbon interface, wherein the contacting is performed at a temperature from about $-100°$ C. to $150°$ C., for a time sufficient to produce a branched, alkylated, paraffinic hydrocarbon.

Figure 1:
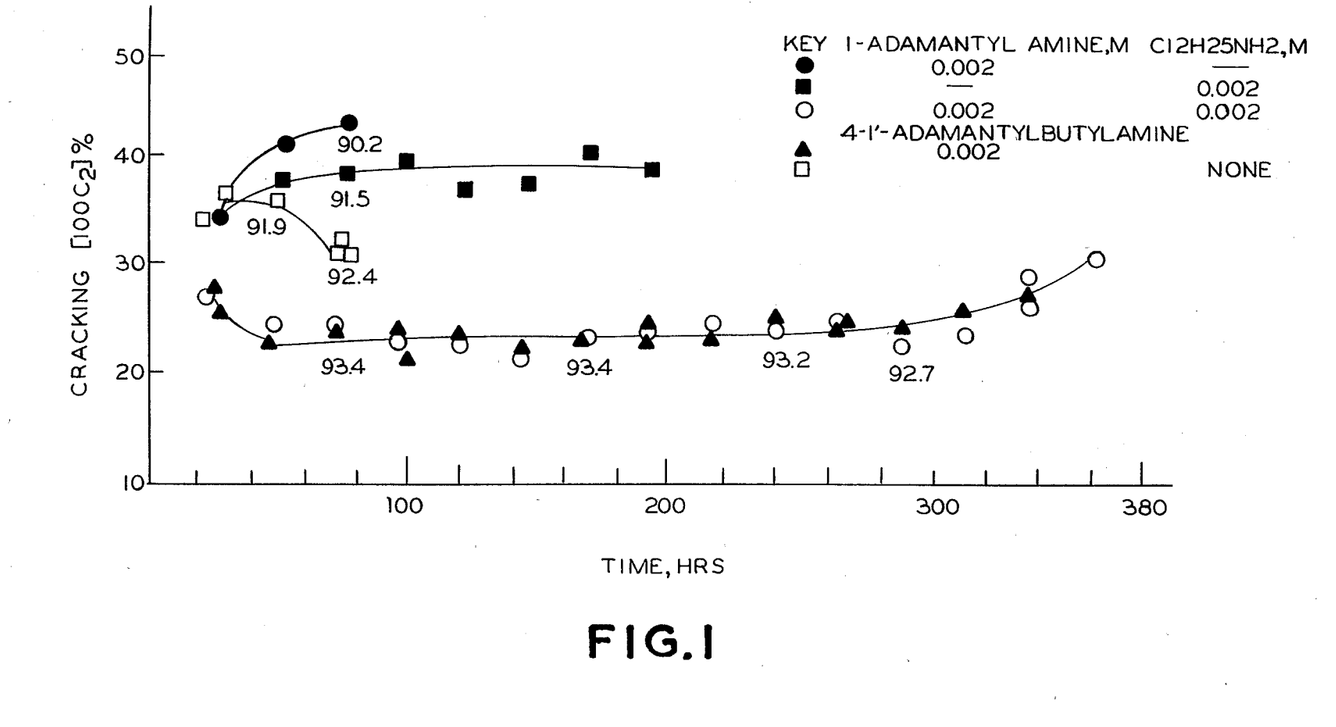
Figure 2:
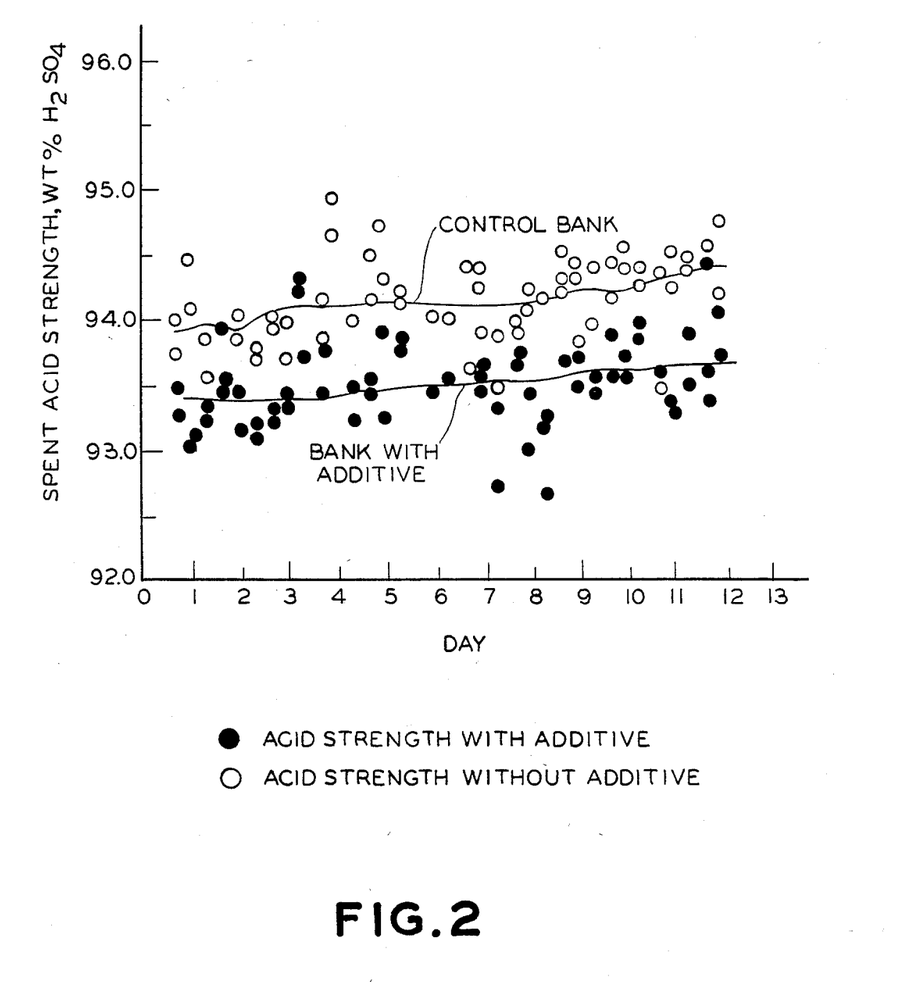
FIG. 2 is a plot of the titrated sulfuric acid strength in two side-by-side alkylation facilities over an extended period of time. One set of data was obtained from an alkylation facility to which no additive was added, while the other set of data was obtained from a facility to which 1-adamantylamine and a mixture of alkylamines was added. The solid lines drawn through each set of data was obtained by a statistical fit of the data.

The alkylation process, if conducted in the presence of either the surfactant, or of an adamantane derivative not having surfactant properties; alone, proceeds relatively poorly, in terms of alkylate quality, yield and catalyst activity maintenance, but proceeds surprisingly well in the presence of a combination of the two. What is particularly surprising is that either agent alone leads to an increase in the degree of cracking obtained while reacting isobutane and isobutylene in a continuous unit with a fixed amount of acid, but that the combination produces an unexpected decrease in the overall amount of cracking. This fact is aptly illustrated in the Figures.

It is believed that adamantane moieties increase the rate of intermolecular hydride transfer between an alkyl carbonium ion (formed by protonation of an olefin) and isobutane or other hydride donors in the system. (These ions are typified by the t-butylcarbonium ion, t-$C_4H_9^+$.) Since intermolecular hydride transfer is generally the rate-determining step in paraffin-olefin alkylation, see "Industrial Laboratory Alkylation", edited by Lyle F. Albright and Arthur R. Goldsby, ACS Symposium Series 55, Published Washington D.C. 1977, Chapter One "Alkylation Studies" by G. M. Kramer) involving hydride transfer from a paraffin to an alkyl or paraffinic carbonium ion, the presence of the adamantane derivative/surfactant combination serves to significantly increase the reaction rate of the desired hydride transfer step in the alkylation process while minimizing the cracking side reactions. In the production of octane-increasing agents, this leads to the formation of more selective products having higher octane numbers, lower acid consumption during the process (which is an important economical and environmental consideration) and affords higher yields through diminished cracking side reactions, which factors enhance the economics of the process.

In preferred embodiments of the present invention the paraffinic compounds contain 4 to 7 carbon atoms and the olefin contains 2 to 6 carbon atoms.

In other preferred embodiments of the present invention the adamantane derivative is represented by the formula Ad—$(CH_2)_n$—X where Ad represents the adamantane ring n=0 to 10, and X is a polar group capable of making the adamantane derivative effectively soluble with the acid throughout the alkylation reaction.

In still other preferred embodiments of the present invention the surfactant has a sufficiently long hydrocarbon group coupled with a polar end group such that critical micelle concentration (CMC) in a strong acid system is less than, or equal to about 0.01M.

BRIEF DESCRIPTION OF THE FIGURES

FIG. 1 illustrates the data in graphical form taken from Example 2 in the specification. (See Example 2 for further details). The graphical data show the extent of cracking versus time for different catalyst systems in the acid catalyzed alkylation of isobutane with isobutene. The different catalyst systems in the sulfuric acid catalyzed alkylation of isobutane with isobutylene which are depicted are: (1) 1-adamantylamine; (2) dodecylamine; (3) mixtures thereof; (4) 4-1'-adamantylbutylamine; (5) a control. As is shown, the catalyst system comprising a mixture of 1-adamantylamine and dodecylamine in 97.8% $H_2SO_4$ gives unexpectedly better results than with either reagent alone, in respect to minimizing the undesirable cracking reaction. The numbers in FIG. 1 are the calculated motor octane numbers (MON) for each alkylate.

DESCRIPTION OF THE INVENTION AND PREFERRED EMBODIMENTS

The reason a mixture of an adamantane derivative, or adamantane moiety, and an appropriate surfactant serves to increase the rate of intermolecular hydride transfer during paraffin-olefin alkylation while minimizing cracking is not totally understood. One theory that we do not wish to be bound by is that reversible hydride transfer from the adamantane moiety to a carbonium ion in solution is enhanced owing to lack of steric repulsions in the translation state involving the adamantane moiety, as compared to hydride transfer involving a paraffinic hydrocarbon and the same carbonium ion.

In many acid systems, including sulfuric acid, the alkylation reaction can occur in either the bulk acid phase or at the hydrocarbon/acid interface. In some systems, it may also occur in the hydrocarbon phase. In sulfuric acid, it is believed that better products are obtained in the interfacial region between the acid and hydrocarbon layers, than in the bulk acid, and consequently, it is desirable to preferentially direct the reaction to this region.

Surface tension measurements, which we have made, indicate that an adamantane derivative, such as adamantylamine, will not lower the surface tension of concentrated $H_2SO_4$ when it is present at concentrations up to 0.01M and consequently, it does not form a stable surface layer. Further, when used under alkylation conditions, the reagent appears to prevent the formation of an emulsion which would otherwise form. The reagent is working as an emulsion breaker, materials which in fact adsorb at interfaces, but in relatively low concentrations and are thought to provide highly mobile surface films rather than stable films characteristic of conventional soaps or surfactants. In order to increase the concentration of this reagent at the acid interface, we believe it should be mixed with another surfactant which has the ability to provide a stable surface film and hence emulsion in the presence of adamantane derivative. At the same time, the surface film will play the role of a conventional soap in drawing carbonaceous material into itself, i.e., extracting the adamantylammonium ion from the acid phase into the polar interfacial region. This should have the effect of markedly increasing the concentration of the adamantane moiety in the surface layer and hence provide the desired means of maximizing the concentration of the hydride transfer catalyst in the region where it is wanted. To increase the concentration of the reagent at the interface and to increase the rate of hydride transfer, it may be desirable to utilize a mixture of surfactants.

In the process, $C_2-C_6$ olefins can be alkylated with $C_4-C_7$ paraffinic compounds, preferably $C_4-C_6$ paraffinic compounds, to produce effective gasoline octane improvement reagents, such as $C_5-C_{11}$ branched paraffinic hydrocarbons. Preferably, the starting paraffinic compound is branched, such as isobutane, which is capable of forming a tertiary carbonium ion under acid conditions. Normal paraffins can be used instead of branched paraffins when the reaction conditions employ a very strong acid medium capable of catalyzing their isomerization to tertiary carbonium ions (except for propane, which forms the secondary isopropyl cations under very strong acid conditions). Representative examples include isobutane, isopentane, 2-methylpentane, 3-methylpentane, 2,3-dimethylpentane, and mixtures thereof. A preferred paraffin in the process is isobutane and preferred is where isobutane is reacted with $C_3-C_6$ olefins to produce $C_7-C_{11}$ branched paraffinic hydrocarbons. Ethylene can also be alkylated, but generally, only with acids which are capable of isomerizing normal paraffins to isoparaffins, e.g., $AlBr_3$.

In the process, carbonium ions can be generated in various ways; in situ from their respective halides, by protonation of an olefin, by oxidation of a paraffin by the acid system, or from a hydrocarbon undergoing an intermolecular hydride transfer reaction with a carbonium ion already present in the acid. The preferred method depends on the acid system, but with $H_2SO_4$ or HF, they are formed readily by protonation of olefins.

Linear or branched $C_2-C_6$ olefins or cyclic olefins useful in the process include ethylene, propylene, butene-1, butene-2, isobutylene, cyclopentene, pentene-1, pentene-2, methylbutenes, hexene-1, hexene-2, 2 methylpentene-2, 2 methylpentene-1, 2,3 dimethylbutene-2, 2,3,dimethylbutene-1, mixtures thereof, and the like. Preferred olefins are butylenes and amylenes, as for example, feeds available from commercial catalytic cracking streams. Particularly preferred are the butylenes.

The weight ratio of paraffin to olefin used in the process generally varies from about 2 to 1 to 20 to 1, and preferably is about 10 to 1. The olefin space velocity is in the range of about 0.01 to 1, preferably 0.01 to about 0.3, liquid volume olefin/liquid volume of acid/hour. A preferred process is where the olefin and paraffin are introduced into the strong acid system as a feedstream mixture.

The product hydrocarbons in the reaction of isobutane with butylenes are alkylates containing mainly $C_8$ branched paraffins. Representative examples include 2,2,4-, 2,3,4-, 2,3,3-, and 2,2,3-trimethylpentanes, 2,4-, 2,3-, and 2,5-dimethylhexanes, and the like. Preferred products in the process are the trimethylpentanes, which are the main products from the alkylation of butylenes.

Product hydrocarbons in the alkylate, from the alkylation of isobutane and propylene are mainly a mixture of dimethylpentanes, and from the alkylation of a mixture of amylenes with isobutane are a mixture of $C_8$ and $C_9$ branched paraffinic hydrocarbons.

Products of the reaction of isobutane with hexenes are a mixture of light paraffins containing $C_5$-$C_{11}$ branched paraffinic hydrocarbons.

The products are useful as gasoline blending agents for octane improvement and/or hydrocarbon solvents.

The phrase "a strong acid system", as used herein, refers to an acid system capable of assisting in generating carbonium ions in the process and includes an "acid component" and a solvent, or a material that can function in both capacities, such as concentrated sulfuric acid, preferably being of initial acid strength of about 90 to 99.8% and preferably about 94 to 99.8 weight percent sulfuric acid, or liquid HF. The acid system can be solid/liquid, liquid or gaseous. Preferably the acid system is a liquid and particularly preferred is concentrated sulfuric acid having an initial acid strength of about 98 weight percent.

The strong acid components in the acid system are conventional protic and aprotic or Lewis acids and include $AlBr_3$, $AlCl_3$, $GaCl_3$, $TaF_5$, $SbF_5$, $AsF_5$, $BF_3$, HF, HCl, HBr, $H_2SO_4$, $HSO_3F$, $CF_3SO_3H$, and the like, and mixtures thereof. Preferred acid components in the process are $H_2SO_4$, HF, $CF_3SO_3H$, or $HSO_3F$. It should be noted that HCl and HBr are preferably not used alone but are used in combination with other Lewis acids, e.g., $AlCl_3$ and $AlBr_3$. Also noted is that in commercial operation the fresh or makeup sulfuric acid is about 98 to 99.5 percent $H_2SO_4$ and the titratable acidity of the "spent" acid is about 90 percent.

Also, an ingredient in the "acid system" may be a solvent, required when the acid component is solid, e.g. $AlBr_3$. For Lewis acids, halogenated paraffins and polyhalogenated aromatics are generally used; representative examples include, but are not limited to $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, concentrated $H_2SO_4$, $HSO_3F$, $CF_3SO_3H$, and the like, and mixtures thereof.

The molar concentration of the Lewis acid in these solvents generally varies from 0.1M to 5.0M and preferably, the range is between 0.5M and 2.0M, based on solvent volume.

The volume ratio of the acid system to the paraffinic hydrocarbon is generally between 5:1 and 1:5 and preferably from 3:1 to 1:3. However, larger and smaller ratios can also be effectively used.

Alkylation reactions are normally carried out in two-phase systems, i.e., an acid phase containing the adamantylamine component acid, and a hydrocarbon phase. However, alkylation processes can also be carried out in partially miscible media which can be formed, for example, from alkanes, $AlBr_3$ and 1,2,3,4-tetrachlorobenzene.

Adamantane derivatives suitable for use in the present invention are those derivatives containing at least one unsubstituted bridgehead position and which are capable of being protonated, or hydrogen bonded to, or dissociated by, the acid, thereby yielding a species which is soluble in acid throughout the alkylation reaction.

It is desirable for most protonic (Bronsted) acid systems that the adamantane derivative not fragment in such a way as to lead to hydrocarbon soluble adamantane moieties which could be extracted from the acid phase by the product stream.

It is to be understood that the adamantane derivatives employed herein may include quaternary salts. Non-limiting examples of such salts include:

where X is any suitable anion.

A preferred class of adamantane derivatives suitable for use herein are those represented by the formula:

where n=0 to 10, and X is a polar group capable of making the adamantane derivative effectively soluble in the acid throughout the reaction.

By effectively soluble we mean that the distribution coefficient $K_D$ of the adamantane moieties in the acid and hydrocarbon phases is such that it can be represented by $$K_D = \frac{[\Sigma \text{adamantane moieties in hydrocarbon phase}]}{[\Sigma \text{adamantane moieties in acid phase}]} < \frac{1}{10^3}$$

preferably $<1/10^5$

Representative examples of polar groups which may be capable of making the adamantane derivative effectively soluble in the acid include groups illustrated on pages 83-96 of "Adamantane: The Chemistry of Diamond Molecules" by R. C. Fert, Jr., publisher, M. Dekker (1976), which is incorporated herein by reference.

Preferred adamantane derivatives are those wherein X contains one or more elements selected from Groups Va, VIa, and VII of the Periodic Table of the Elements as illustrated in the inside cover of the Handbook of Chemistry and Physics, CRC Press, 55th edition, 1976. More preferred is when X contains one or more elements selected from Groups Va and VIa, most preferred is when X contains one or more of N, O, P and S, particularly N. Also most preferred are adamantane derivatives wherein X is selected from the group consisting of $-PH_2$, $-NO_2$, $-SH$, $-C\equiv N$, $-COOH$, $-SO_3H$, and $-NH-COCH_3$.

Another preferred class of adamantane derivatives suitable for use herein can be represented by the formula:

$$Ad-(CH_2)_n-XR^1R^2$$

where $n = 0$ to $10$, X is a Group Va element such as N or P, preferably N, and $R^1$ and $R^2$ are independently selected from H and $C_1-C_{18}$ linear alkyl groups, preferably $C_1-C_{12}$ alkyl, wherein said $C_1-C_{18}$ linear alkyl groups can be substituted with inert or unreactive substituents under the process conditions with the proviso that the substitution does not result in a tertiary carbon-hydrogen bond. Also included are compositions where X is a Group VIa element, such as sulfur. In such a case, the above formula can be written $Ad-(CH_2)_n-XR^1$, wherein n and $R^1$ are defined above.

Yet another preferred class of adamantane derivatives are heteroadamantane derivatives containing one or more heteroatoms wherein the heteroatoms are selected from Groups IVa, Va and VIa of the Periodic Table of the Elements, preferably P, N, and S, more preferably N. Representative examples of such compositions are found on pages 267–317 of "Adamantane: The Chemistry of Diamond Molecules" Id.

It is to be understood that the adamantane ring itself can be further modified and substituted with groups on the bridgehead or non-bridgehead positions which are inert or unreactive under the process conditions and include: $C_1-C_4$ alkyl and alkoxy groups, provided no tertiary CH bonds are present; $NO_2$; and $CF_3$ or $C_nF_{2n+1}$ (where $n = 1-10$) as replacements for the remaining protons provided that at least one adamantyl bridgehead hydrogen remains to promote intermolecular hydride transfer.

Where both $R^1$ and $R^2$ are alkyl, the nitrogen atom of the amine may be further substituted with still a third alkyl group, $R_3$, being a $C_1-C_{18}$ linear alkyl and having the same general description given above for $R^1$ and $R^2$, and also being chosen independently therefrom, resulting in a quaternary ammonium ion, associated with a suitable anion, being soluble in sulfuric acid and chemically inert under the reaction conditions. Suitable anions include: sulfate; bisulfate; halide, e.g. chloride, bromide, iodide; acetate, and the like. Preferred anion is sulfate in the process.

The amino group of a most preferred adamantane derivative adamantylamine, used in the process can thus be unsubstituted, i.e., $-NH_2$; N-monosubstituted, e.g., $-NHR^1$; N,N-disubstituted, i.e., $-NR^1R^2$; or quaternary, i.e., $-N^+R^1R^2R^3$. Preferred in the process is the N-unsubstituted 1-aminoadamantane.

Representative examples of adamantylamines include 1-adamantylamine, 2-adamantylamine, 3-methyl-1-adamantylamine, N-methyl-1-adamantylamine, N,N-dimethyl-1-adamantylamine, N-t-butyl-1-adamantylamine, N-methyl-N-propyl-1-adamantylamine, N,N,N-trimethyl-1-adamantylammonium sulfate, and the corresponding iodide, 3-methyl-5-ethyl-1-adamantylamine, 3,5-dimethyl-1-adamantylamine, 3-methyl-1-adamantylamine, 1,3-adamantyldiamine, 3-methylamine-1-adamantylamine and the like. A preferred catalyst compound is 1-adamantylamine.

It should also be noted that readily solvolyzed derivatives of these amines including their amides, carbamates, ureas, thio derivatives thereof, and the like, which generate the corresponding free amine, and the resulting ammonium salt thereof, in acidic media, through solvolysis, or are reversibly protonated under "protic acid" reaction conditions, can also be used in place of the parent adamantylamine compounds and are included within the scope of the claimed subject process. Further, salts such as the ammonium and alkyl ammonium salts of the above-described unsubstituted, N-monosubstituted and N,N-disubstituted adamantylamines can be directly employed containing anions such as the chloride, sulfate, acetate, and the like, as described hereinabove for the quaternary nitrogen compounds.

Although the polar, or functional group, of the adamantane derivatives employed herein may be bonded to a non-bridgehead as well as a bridgehead carbon it is preferred that it be bonded to a bridgehead carbon.

The molar concentration of adamantane derivative in the acid solution varies from about $10^{-6}$ to $10^{-1}$ moles/liter, and preferably about $10^{-4}$ to $10^{-2}$ moles/liter. However, larger and smaller ratios can also be used effectively.

Surfactants suitable for use herein are those compositions containing a non-polar hydrocarbon portion end and a polar end which compositions are capable of stabilizing the adamantane moieties at the acid-hydrocarbon interface, such that its concentration can be measured and the alkylation process is substantially improved. The stability of the adamantane moieties at the interface can, of course, be measured by any suitable conventional technique such as by synthesizing the adamantane derivative in such a way to incorporate thereon a radioactive carbon atom as a tracer. The concentration of the tagged adamantane derivative at the interface can then easily be determined by measuring the radioactivity in that area.

The surfactants used herein should also be such that they will undergo no substantial degradative side reactions such as: (1) losing their polar end groups, (2) cracking of their hydrocarbon chains, or (3) deleterious oxidative reactions. Furthermore, it is preferred that the surfactants have a sufficiently long alkyl, or hydrocarbon, group coupled with a polar end group such that the molecule has surfactant properties in strong acid systems at concentrations less than about 0.01M.

The inventors hereof have found that the surface activity of molecules is similar in concentrated $H_2SO_4$ and in water.

It is preferred that the surfactant of the present invention be reversibly protonated having an equillibrium constant K for the reaction:

$$RX + H^+ \rightleftharpoons RX^+H$$

where $$K = \frac{[RX^+H]}{[RX][H^+]} \geq 10$$

It is also preferred that the surfactants used herein be cationic surfactants.

Specifically preferred surfactants include the $C_6-C_{18}$ alkyl phosphenes, $C_6-C_{18}$ dialkyl sulphides, $C_6-C_{18}$ alkyl mercaptans, $C_6-C_{18}$ alkyl carboxylic acids, $C_6-C_{18}$ alkyl sulfonic acids, $C_6-C_{18}$ alkyl phosphonic acids, and $C_6-C_{18}$ alkyl amines. More preferred are the alkyl amines.

The surfactants can be primary, secondary, or tertiary in structure, and can be prepared by conventional methods in the art. The particular surfactant utilized may be dependent on many factors including olefin and paraffin feed composition, acid system, specific alkylation equipment utilized, and desired alkylate properties.

The hydrocarbon chains of the surfactants can be substituted with inert substituents, in like manner, as the alkyl R groups described above for adamantylamine, with the same proviso that the substitution does not result in the inclusion of a tertiary carbon-hydrogen bond.

The preferred alkyl amines may also include long chain amine moieties which may contain more than one substituted or unsubstituted amino group, with the proviso that said long chain amino moiety exhibit surfactant properties under the process conditions. One example of such long chain amino moiety is a long chain substituted ethylene diamine, e.g., N-hexadecyl-N,N',N'-trimethyl-ethylenediamine. Quaternary salts formed from the compound are also operable and included within the scope of the invention, e.g, the corresponding methylammonium salt of the above-recited hexamethyl trimethylethylenediamine compound.

The long chain paraffinic amines can be unsubstituted on the amino group or be N-substituted by $C_1$–$C_{18}$ alkyl groups, with the proviso that said alkyl groups don't contain tertiary C—H bonds. The unsubstituted amine or N-methyl substituted amines are preferred.

The amine group in the long chain amine compounds can also be trisubstituted with said alkyl groups forming quaternary ammonium compounds with an associated anion. Applicable anions are the same as described above for the quaternary ammonium adamantyl compounds. A preferred long chain alkylamine in the process is a $C_6$–$C_{12}$ linear alkylamine.

Representative long chain alkyl amines include n-hexylamine, n-heptylamine, n-octylamine, n-nonylamine, n-decylamine, n-dodecylamine, n-laurylamine, n-myristylamine, n-stearylamine, neohexylamine, N-methyl-n-hexylamine, N,N-dimethyl-n-hexylamine, N-methyl-N-ethyl-n-octylamine, N,N,-N-trimethyl-n-hexyl-ammonium sulfate, N',N',N-trimethyl-N-hexadecyle-thylenediamine, and its methyl ammonium sulfate salt thereof, their neo-isomers, mixtures thereof, and the like. Preferred amines in the process are n-octylamine, n-decylamine, and n-dodecylamine.

The molar ratio of surfactant to the adamantane derivative used herein is in the range of about 1:100 to 10:1 and generally corresponds to a weight ratio of about 1:100 to 10:1. Preferably, a molar ratio of about 1:100 to 2:1 and particularly preferred, a 1:10 to 1:1 molar ratio is used.

When the adamantane derivative itself can act as its own surfactant, the importance of an additional surfactant may be minimized or not required at all. For example, if the adamantane derivative is 4-[1'-adamantyl]-butyl amine, which is a good catalyst itself its performance may be enhanced by adding an additional surfactant which can increase the surface density of the adamantyl species at the interface.

If the olefin/paraffin feed requires a stronger surfactant than used for isobutane/isobutene, then either a longer chain amine, i.e., $C_{14}$–$C_{16}$ alkylamine, or higher concentrations of the shorter $C_6$–$C_{12}$ amine should be employed.

It is further understood that mixtures of adamantane derivatives, described above, and mixtures of surfactants, described above, may be used in the process and catalyst composition described herein. For example, a mixture of surfactants may be desirable to provide the desired emulsifying qualities and the desired hydride transfer rate.

Temperatures in the process are conducted in the range of about −100° to 150° C. and preferably about −50° to 100° C., depending primarily on the temperature required to obtain a liquid-phase catalyst. A particularly preferred temperature range in concentrated sulfuric acid is −10° C. to 30° C.

The process is normally carried out at atmospheric pressure but may also be conducted at higher pressures up to about 20 atmospheres, the pressure depending primarily on the partial pressure of isobutane in the reaction mixture.

Yields of paraffinic branched hydrocarbons in the process range from about 80 to 100 percent of theory, based on starting olefin. Theoretical yield is calculated from the equation:

$$\text{Theo.Yield} = \frac{\text{gms. alkylate produced} \times 100}{\text{gms. olefin fed}}$$

The theoretical yield in the process of alkylating butylenes, with isobutane, on this basis, is 204%.

Particularly preferred embodiments of the process are where butene-1, butene-2, or isobutylene is reacted with isobutane to produce predominantly a mixture of 2,2,4-, 2,3,4-, 2,3,3- and 2,2,3-trimethylpentanes; where propylene is reacted with isobutane to produce a $C_7$ product comprising 2,3- and 2,4-dimethylpentanes; where isobutane is reacted with a mixture of propylene, butylene and amylenes as obtained from refinery streams, to produce a mixture comprising of 2,3- and 2,4-dimethylpentanes, 2,2,4-, 2,3,4-, 2,3,3-, and 2,2,3-trimethylpentanes, branched $C_8$ and branched $C_9$ paraffinic hydrocarbons; where isobutane is reacted with a mixture of butenes, as obtained from a petroleum commercial cracking feedstream, to produce a mixture comprising branched $C_8$ paraffinic hydrocarbons, of which about 80 percent can be trimethylpentanes; and where isobutane is reacted with a mixture of amylenes, as obtained from a petroleum commercial cracking feedstream, to produce a mixture comprising predominantly branched $C_8$ and branched $C_9$ paraffinic hydrocarbons.

Apparatus for carrying out the subject process is conventional, either on a laboratory, pilot plant, or full industrial scale and the process can be conducted in a batch-type operation or in a continuous-type operation and in liquid/liquid or liquid/gas systems. The adamantylamine may also be used in solid/liquid or solid/gas systems, wherein its polar functionality is adsorbed onto or bound by a highly acidic solid acid. The amine can be conveniently used in the form of its ammonium salt, i.e., as the ammonium sulfate, when working with sulfuric acid. A preferred type of process is a liquid/liquid system conducted in a continuous manner.

Generally, the process is conducted by contacting a mixture of paraffin and olefin with a liquid strong acid system containing a mixture of an adamantane derivative such as an adamantylamine and one or more surfactants such as the $C_6$–$C_{18}$ long chain alkylamines. If the strong acid system is, for example, concentrated $H_2SO_4$, then the process is conducted in an emulsion of the two-phase system, the acid system usually being the continuous phase although this is not essential to the process. The entire system is preferably at reaction temperature at time of mixing, during which the entire system is vigorously mixed, stirred and agitated to insure good contact between the acid and hydrocarbon phases. The reaction mixture in a commercial reactor is normally transferred to a settler in which the acid and hydrocarbon phases separate on standing. The acid is usually recycled to the reactor after a small portion is drawn-off and replaced with fresh acid. The replacement rate is determined by the extent of acid consumption which can be determined by standard titration procedures.

The hydrocarbon phase is essentially isobutane containing heavier hydrocarbons, which is the alkylation product. This is normally distilled to afford isobutane which is recycled to the reactor, a gasoline boiling range, high octane fraction and heavier fractions which may be used as solvents. The octane number of the gasoline boiling range fraction or "alkylate" can be determined by standard procedures including gas chromatographic analysis.

A preferred surfactant/hydride transfer catalyst composition of the present invention is a mixture of (a) an adamantylamine, containing at least one unsubstituted bridgehead carbon atom as the hydride transfer catalyst; and (b) one or more $C_6-C_{18}$ alkylamines as the surfactant.

The surfactant/hydride transfer catalyst composition mixture, which can be an admixed solid, slurry or solution, is useful in the paraffin-olefin alkylation process described herein in which the composition can display synergistic catalyst effects particularly with respect to decreased cracking and acid consumption versus the use of either the adamantane derivative or the surfactant, alone, in the process.

The adamantane derivatives and the surfactants suitable for use herein are already described hereinabove, in reference to general characteristics and preferred species and including reference to manner of making and using and need not be further reiterated herein. The composition can be made ex situ from the sulfuric acid solution by mixing the components together resulting in a solid, slurry or solution depending on the physical nature of the components. Alternately the composition can be made in situ by dissolving the components separately in sulfuric acid solution of the acid strength described herein.

A preferred adamantane derivative, adamantylamine, in the composition is 1-adamantylamine, or salt thereof. Preferred alkylamines are octyl-, decyl- and dodecylamines, salts thereof, or mixtures thereof. As discussed in more detail hereinafter, a particularly preferred mixture of alkylamines comprises a mixture of octyl- and dodecylamines. The molar ratio of the octylamine to the dodecylamine may range between about 100:1 to about 1:3, preferably between about 30:1 to about 1:1. Particularly preferred alkylammonium salts are the alkylammonium sulfates, although other alkyl ammonium salts may also be useful.

Particularly preferred compositions are 1-adamantylamine/n-octylamine; 1-adamantylamine/n-decylamine; 1-adamantylamine/n-dodecylamine; and 1-adamantylamine/n-octylamine and n-dodecylamine in the above-stated molar ratios.

A further subject of the invention is an aqueous sulfuric acid solution of 60-99.8% $H_2SO_4$ acid strength, and preferably 75-99.8% $H_2SO_4$ acid strength, comprising the surfactant/hydride transfer catalyst composition described above, useful in hydride transfer processes. Particularly preferred is where said solution is used in paraffin-olefin alkylation, wherein the sulfuric acid strength is 90-99.8% and preferably 94-99.8% acid strength. The 60-90% acid solutions can also be used for blending with concentrated sulfuric acid solutions in the paraffin-olefin alkylation.

A preferred embodiment is where the composition is present in a molar concentration of $10^{-6}$ moles to $10^{-1}$ moles per liter, on the basis of the adamantane derivative and the surfactant components, in the sulfuric acid solution.

Also a preferred embodiment is where the 90-99.8% sulfuric acid solution is used in paraffin-olefin alkylation and contains dissolved olefin, e.g., linear or branched $C_2-C_6$ olefin and dissolved, admixed, or emulsified paraffin, e.g., $C_4-C_7$ paraffinic compounds capable of being alkylated with said olefin.

It is to be understood that obvious modifications and variations on the above-described procedure, subject process and composition, not specifically described herein, are deemed to be encompassed within the general scope and spirit of the application.

The following examples are illustrative of the best mode of carrying out the invention, as contemplated by us, and should not be construed as being limitations on the scope or spirit of the instant invention.

EXAMPLE 1

This Example illustrates the positive synergistic effect of the use of the combination of adamantylamine/long chain fatty amine as a catalyst on the alkylation of isobutene with isobutene. The runs were conducted by passing a continuous liquid mixture stream containing 90 weight percent isobutane and 10 weight percent isobutene (olefin liquid hourly space velocity of 0.1/v/v/hr.) through 10 ml. 97.8 percent sulfuric acid in an externally cooled glass reactor with vigorous agitation. The temperature of the contents in the glass reactor was maintained at 10° C. and the process was conducted at about 40 psig pressure. In both the additive and blank runs, pure isobutane was initially passed through the acid in order to fill the reactor within several minutes. After this time, the olefin-containing feed was used and the rate was adjusted so that a steady state rate of 1 ml of olefin per hour and 9 ml of isobutane per hour was maintained thereafter. As the liquid hydrocarbon stream contacted the acid, an emulsion was visibly formed. This consisted of a lower acid continuous phase of about 20 to 30 ml. in volume and an upper phase of isobutane. As the alkylation reaction progressed, the alkylate product which was formed in the emulsified region migrated into the upper isobutane layer from which it exited the glass reactor through a control valve. The volume of the upper layer was about 50 ml. The process was allowed to run for several hundred hours with the product being sampled periodically for gas chromatographic analyses, from which the alkylate selectivity (percent of $C_8$ components in the $C_5$ to first major $C_9$ component), MON (motor octane number, clear), yield and extent of cracking could be deduced. The runs using the adamantylamine and long chain amine were carried out with each present in the sulfuric acid layer at a concentration of $2 \times 10^{-3}$M. The control was run in the absence of an adamantylamine. The results are illustrated in tabular form below in Table I. The extent of cracking, expressed as [100-$C_8$]%, is the % of liquid hydrocarbons in the product alkylate, other than the expected $C_8$ materials, in which the $C_8$-excluded materials range from pentanes to trimethylhexanes, as determined by gas chromatographic analysis.

TABLE I

| Acid Catalyst | Extent of Cracking, % [100-% C$_8$] in Alkylate[b] |
|---|---|
| 97.8% H$_2$SO$_4$ | 36 |
| 97.8% H$_2$SO$_4$ + adamantylamine[a] | 39 |
| 97.8% H$_2$SO$_4$ + dodecylamine[a] | 36 |
| 97.8% H$_2$SO$_4$ + combination of AA[a] + DDA[a] | 24 |

[a]concentration of 2 × 10$^{-3}$ M;
[b]sampling times at about 40 hours.

As is seen from the data, the mixture of adamantylamine with dodecylamine significantly lowered the extent of cracking when compared to that of the individual reagents used alone.

EXAMPLE 2

Utilizing the apparatus and the general procedure described in Example 1 using 97.8% H$_2$SO$_4$, an olefin liquid space velocity of 0.1/v/v/hr. at the same 9:1 volume ratio of isobutane/isobutene at 10° C. and 40 psig pressure, the reaction was carried out continuously for each of the following catalyst systems in overall total time periods ranging from 50 to about 350 hours, using the following reagents in 2×10$^{-3}$M quantities: (a) 1-adamantylamine (AA); (b) dodecylamine (DDA); (c) mixture of AA/DDA; (d) 1'-adamantyl-4-butylamine (ABA). Table II lists below the resulting data in tubular form as derived from gas chromatographic analysis. The data is also presented in graphic form in FIG. 1.

TABLE II

Extent of Cracking in Alkylate, [100-% C$_8$], %

| Time (Hours) | AA | DDA | AA/DDA | ABA |
|---|---|---|---|---|
| 0 | 36 | 35 | 25 | 24 |
| 30 | 41 | 38 | 24 | 22 |
| 50 | 43 | 38 | 24 | 23 |
| 70 | — | 38 | 24 | 23 |
| 90 | — | 38 | 24 | 23 |
| 110 | — | 38 | 24 | 23 |
| 130 | — | 38 | 24 | 23 |
| 150 | — | 38 | 24 | 23 |
| 170 | — | 38 | 24 | 23 |
| 190 | — | 38 | 24 | 23 |
| 230 | — | — | 24 | 23 |
| 270 | — | — | 24 | 24 |
| 310 | — | — | 24 | 25 |
| 350 | — | — | 29 | 25 |

The tabulated data are observations which were made at steady state conditions after an initial induction or conditioning period which lasted about 10 to 20 hours. Such periods are known and commonly observed during alkylation and are believed to relate to the buildup of reaction intermediates to a steady state concentration.

The tabulated data shows the extent of cracking observed at various times during the continuous alkylation experiments. This is a measure of the selectivity of the reaction to desired products. Low cracking indicates more selective conversion of the reactants to the desired products.

When either adamantylamine or dodecylamine was used separately, the product was found to contain a relatively high proportion of cracking components. However, when these additives were combined, the extent of cracking was substantially repressed. The resulting product contained a significantly increased amount of the desired C$_8$ compounds.

As a consequence of the improved alkylation reaction, other parameters indicative of catalyst performance were also found to be helped. One of these parameters is the alkylate yield; defined as:

$$\text{Alkylate yield} = \frac{\text{wt. \% alkylate in product}}{\text{wt. \% olefin in reactants}} \times 100$$

This parameter, which has a theoretical value of 204 for butylene alkylation, never exceeded a value of 100 in the run with adamantylamine. It did not exceed a value of 150 in the run with dodecylamine but fell to a value of about 100 in about 100 hours. By contrast, in the run with the adamantylamine/dodecylamine mixture, the alkylate yield remained (within experimental error) at the theoretical level for the duration of the run which lasted 360 hours.

The performance of the adamantylamine/dodecylamine mixture was nearly identical to that achieved with the use of 4-1'adamantylbutylamine alone. This aminoalkyladamantane behaves as a normal surfactant in H$_2$SO$_4$ by lowering its surface tension. It has previously been shown by us that it improves the above-described alkylation reaction. Adamantylamine by itself, does not measurably lower the surface tension of concentrated sulfuric acid, and does not measurably aid the alkylation process. The above runs show, however, that adamantylamine in combination with dodecylamine, a known surfactant which can provide a stable surface film in the process, exerts a synergistic effect in promoting the alkylation, as witnessed by the increased longevity of the process, resulting in significant savings in acid life in the process, together with a substantial and unexpected decrease in the degree of cracking.

The above runs were repeated under substantially the same conditions using decylamine (C$_{10}$), myristylamine (C$_{14}$) and stearylamine (C$_{18}$) in place of dodecylamine. It was found that decyl- and myristylamine gave substantially equivalent results to the dodecylamine, and that all these gave slightly better overall results than the stearylamine, including resulting octane quality, degree of cracking, and acid consumption. N-octylamine (C$_8$) employed at 0.0005M concentration gave similar results.

EXAMPLE 3

This example demonstrates the utility of 1-adamantylamine in combination with a mixture of n-octylamine and n-dodecylamine in sulfuric acid catalyzed alkylation. A side-by-side simultaneous 12 day test was conducted in a continuous alkylation unit during which one alkylation facility had no adamantylamine or alkyl amine present, while the other facility had a steady state concentration of about 0.0005 molar 1-adamantylammonium sulfate, 0.001 molar octylammonium sulfate and 0.0001 molar dodecylammonium sulfate, in the sulfuric acid. In this test the olefin feed comprised approximately 50 weight percent propylene and 50 weight percent butylene while the paraffin comprised approximately 75 weight percent isobutane and 25 weight percent n-butane. The acidity in the additive reactor train initially was about 0.5 percent lower than in the control reaction train to which no additive was added. Based upon a statistical fit of the data shown in FIG. 2 which took into account small differences in the feed rates and the occasional presence of acid consuming feed impurities in both reactor trains, this slightly lower acidity in the additive side of the unit was maintained even though the acid replacement rate to the reactor train containing the adamantylamine additive was only about 70 percent of that to the "control" reactor train. Based upon this data it is believed that at least a 20% savings in acid consumption could be realized. In addition, analysis of the alkylate produced indicated that the use of the adamantane and alkylamine additives may have improved the octane and yield of the alkylate as compared to the alkylate produced by the facility to which the adamantane and alkylamine had not been added.

What is claimed is:

1. An alkylation process comprising the step of contacting a paraffinic compound, capable of forming a carbonium ion under strong acid conditions, with an olefin in the presence of a strong acid system comprised of an acid component and a mixture of:
   (a) one or more adamantane derivative containing at least one unsubstituted bridgehead position and which is capable of being protonated, or hydrogen bonded to, or dissociated by an acid; and
   (b) one or more surfactants capable of stabilizing the one or more adamantane derivatives of (a) above at a hydrocarbon-acid interface.

2. The process of claim 1 wherein the adamantane derivatives are represented by the formula $$Ad-(CH_2)_n-X$$

where $n=0$ to 10, and X is a polar group capable of making the adamantane derivative soluble in a strong acid system.

3. The process claim 2 wherein X is selected from the group consisting of $-PH_2$, $-NO_2$, $-SH$, $-C\equiv N$, $-COOH$, $-SO_3H$ and $-NH-COCH_3$.

4. The process of claim 1 wherein the catalyst composition can be represented by the formula:

$$Ad-(CH_2)_nXR^1R^2$$

where $n=1-10$, X is N or P, and $R^1$ and $R^2$ are independently selected from H and $C_1-C_{18}$ linear alkyl groups, in which said linear alkyl groups can independently be substituted with inert or unreactive substituents under the process conditions, with the proviso that said substitution does not result in a tertiary carbon-hydrogen bond, and where $R^1$ and $R^2$ are said alkyl as above in the formula.

* * * * *